United States Patent [19]

Baizer et al.

[11] Patent Number: 4,798,818

[45] Date of Patent: Jan. 17, 1989

[54] CATALYST COMPOSITION AND PROCESS FOR ITS PREPARATION

[75] Inventors: William X. Baizer; Robert L. Bixler, Jr.; Michael D. Meddaugh, all of Midland; Antony P. Wright, Mills Township, Gladwin County, Mich.

[73] Assignee: Dow Corning Corporation, Midland, Mich.

[21] Appl. No.: 125,901

[22] Filed: Nov. 27, 1987

[51] Int. Cl.$^4$ .................... B01J 27/12; B01J 27/128; B01J 27/132; B01J 27/135

[52] U.S. Cl. ............................... 502/228; 502/227; 502/229; 502/231

[58] Field of Search ............... 502/227, 228, 229, 231; 570/155, 160

[56] References Cited

U.S. PATENT DOCUMENTS

| | | | |
|---|---|---|---|
| 2,669,590 | 2/1954 | Miller et al. | 260/653 |
| 2,787,646 | 4/1957 | Haszeldine | 260/653 |
| 2,889,379 | 6/1959 | Ruh et al. | 260/653.4 |
| 3,178,483 | 4/1965 | Christoph et al. | 260/653.4 |
| 3,178,484 | 4/1965 | Christoph et al. | 260/653.4 |
| 3,650,987 | 3/1972 | Vecchio et al. | 252/442 |
| 3,739,036 | 6/1973 | Valicenti et al. | 260/653.3 |
| 3,752,850 | 8/1973 | Scherer et al. | 260/544 F |
| 4,078,007 | 3/1978 | Ferstandig | 260/653.7 |
| 4,138,355 | 2/1979 | Ferstandig | 252/182 |
| 4,147,733 | 4/1979 | Fiske et al. | 260/653.4 |
| 4,220,608 | 9/1980 | Feiring | 260/653.3 |
| 4,465,786 | 8/1984 | Zimmer et al. | 502/169 |

FOREIGN PATENT DOCUMENTS

| | | |
|---|---|---|
| 0042696 | 11/1983 | European Pat. Off. . |
| 0074069 | 1/1986 | European Pat. Off. . |
| 63650 | 10/1965 | Japan . |
| 133308 | 12/1974 | Japan . |
| 144509 | 12/1978 | Japan . |
| 16943 | 1/1985 | Japan . |
| 823519 | 11/1959 | United Kingdom . |
| 1283386 | 7/1972 | United Kingdom . |

OTHER PUBLICATIONS

Pierce et al., Industrial and Engineering Chemistry, 52 (Sep., 1960), pp. 783–784.

*Primary Examiner*—W. J. Shine
*Attorney, Agent, or Firm*—Carl A. Yorimoto

[57] ABSTRACT

What is described is a process for preparing a more effective catalyst for the vapor-phase reaction of 1,1,1,3-tetrachloropropane with anhydrous hydrogen fluoride to produce 3,3,3-triflurorpropene-1. The process comprises (A) mechanically mixing, in the absence of water, of (i) aluminum fluoride which has been prepared at temperatures less than about 400° C. and (ii) a transition metal compound, the transition metal compound being selected from a group consisting of compounds of cobalt, chromium, iron, manganese, nickel, titanium, and vanadium; and (B) contacting the mechanical mixture with sufficient anhydrous HF to convert the transition metal compound to a transition metal fluoride. Also described is the catalyst. Additionally, a process for the preparation of 3,3,3-trifluoropropene-1 in which the catalyst is utilized is described.

18 Claims, No Drawings

CATALYST COMPOSITION AND PROCESS FOR ITS PREPARATION

BACKGROUND OF THE INVENTION

This invention relates to the preparation of 3,3,3-trifluoropropene-1 via the reaction of a 1,1,1,3-tetrahalopropane and anhydrous hydrogen fluoride. More specifically, this invention relates to the preparation of 3,3,3-trifluoropropene-1 in which a simpler, improved catalyst than has been previously known in the art is utilized, 3'3,3-trifluoropropene-1 (TFP) is a chemical intermediate that has significant value as a commercial raw material. A primary example of the commercial value of TFP is its use in the preparation of fluorosilicone intermediates and such final products as fluorosilicone fluids and fluorosilicone rubber. Pierce et al., *Industrial and Engineering Chemistry*, 52(September, 1960), pp. 783–784, outline the preparation of the fluoroalkyl-substituted polydiorganosiloxane intermediates utilized in fluorosilicone materials, starting with TFP.

Haszeldine, U.S. Pat. No. 2,787,646. issued Apr. 2, 1957, discloses a process for the preparation of 3.3.3-trifluoropropenes from the fluorination of halogenpropenes. Suitable fluorinating agents disclosed are antimony trifluoride, antimony trifluorodichloride. The reaction occurs at low temperature in a liquid phase.

British Patent, G.B. No. 823,519, published Nov. 11, 1959, discloses the preparation of TFP from the reaction of 1,1,3-trichloropropene-1 with anhydrous hydrogen fluoride in the presence of a fluoride of vanadium, manganese, iron, cobalt, nickel, titanium, or silver at a temperature of at least 150° C. This reference also teaches the impregnating of supports such as alumina, calcium oxide and aluminum fluoride with aqueous solutions of the metal fluorides. Also cited as catalysts are oxyfluorides and complex salts such as hexafluorotitanates.

Valicenti et al., U.S. Pat. No. 3,739,036, issued June 12, 1973, discloses a process for the preparation of TFP by contacting a halogenated hydrocarbon, such as 1,1,1,3-tetrachloropropane, with sodium fluoride at a temperature of from 400° to 475° C.

Ferstandig, U.S. Pat. No. 4,078,007, issued Mar. 7, 1978, and Ferstandig, U.S. Pat. No. 4,138,355, issued Feb. 6, 1979, disclose a process for the preparation of 3-chloro-1,1,1-trifluoropropane from the reaction of a 1,1,1,3-tetrahalopropane and liquid anhydrous hydrogen fluoride in the presence of a mixture of antimony pentahalide and antimony trihalide. The resultant 3-chloro-1,1,1-trifluoropropane is reacted with alkali to yield TFP.

Feiring, U.S. Pat. No. 4,220,608, issued Sept. 2, 1980, discloses the preparation of TFP by reaction of either 1,1,1,3-tetrachloropropane, 1,1,3-trichloropropene-1, or 3,3,3-trichloropropene-1 with anhydrous hydrogen fluoride under autogenous pressure in the presence of at least a catalytic amount of an organic monoamine, a salt of a monoamine, or an alkylene diamine.

Chromium oxyfluorides are cited in the art as catalysts for the preparation of TFP via the vapor phase reaction of halogenated hydrocarbons with anhydrous hydrogen fluoride. Ruh, U.S. Pat. No. 2,889,379, issued June 2, 1959, discloses a process in which a chromium oxyfluoride catalyst is used. Ruh presents an example of the preparation of a chromium oxyfluoride catalyst in which basic chromium fluoride and hydrated aluminum fluoride are slurried in aqueous hydrogen fluoride. Sugar is added to the slurry, and the slurry is dried to a cake. The cake is pelletized and contacted with oxygen for four hours at 550° C. Zimmer et al., U.S. Pat. No. 4,465,786, issued Aug. 14, 1984, discloses a similar catalyst preparation. However, the preparation disclosed by Zimmer et al., involves the simultaneous fluorination of chromium and aluminum oxides in a manner similar to that taught by Ruh. Scherer et al., U.S. Pat. No. 3,752,850, issued Aug. 14, 1973, discloses fluorination of aliphatic hydrocarbons with anhydrous hydrogen fluoride at elevated temperatures in the presence of a catalyst with an empirical formula between $CrF_{1.5}O_{1.5}$ and $CrF_2O$.

This catalyst is prepared by fluorinating $Cr(OH)_3$ with anhydrous hydrogen fluoride at 400° C.

Three references cite the activation of fluorination catalysts by addition of chlorine or chlorinated ethanes in the preparation of TFP. Japanese OPI No. 133,308/74, published Dec. 21, 1974, discloses the preparation of TFP from 1,1,1,3-tetrachloropropane and hydrogen fluoride in the presence of a fluorination catalyst, hexachloroethane and 1,1-dichloroethane being present in the reaction. Japanese OPI No. 144,509/78, published Dec. 15, 1978, discloses the preparation of TFP by the vapor phase reaction of 1,1,1,3-tetrachloropropane with hydrogen fluoride in the co-presence of a fluorination catalyst and hexachloroethane or 1,1-dichloroethane, the reactants being passed through a catalyst bed and then through a catalyst bed of vapor fluorination catalyst. U.S. Pat. No. 4,465,786, Zimmer et al., issued Aug. 14, 1984, discloses that fluorination catalysts can be activated by contact of the catalyst with chlorine or pentachloroethane.

Several references, not citing the preparation of TFP, cite the use of aluminum fluoride as a catalyst for the fluorination of halogenated hydrocarbon materials. U.S. Pat. No. 2,669,590, Miller et al., issued Feb. 6, 1954. discloses the use of essentially non-crystalline aluminum fluoride as a catalyst for the reaction of a two-carbon olefin containing the $=CF_2$ group with hydrogen fluoride to yield fluorine-containing ethanes. U.S. Pat. No. 3,178,483, Christoph et al., issued Apr. 13, 1965, and U.S. Pat. No. 3,178,484, Christoph et al., issued Apr. 13, 1965, disclose the reaction of acetylene with hydrogen fluoride in the presence of beta- or gamma-aluminum fluoride to produce vinyl fluoride and 1,1-difluoroethane. Japanese Pat. No. 498,015, published Feb. 2, 1967, discloses the vapor-phase reaction of acetylene in the presence of amorphous aluminum fluoride to produce vinyl fluoride and 1,1-difluoroethane.

U.S. Pat. No. 3,650,987, Vecchio et al., issued Mar. 21, 1972, discloses the preparation of fluorinated ethanes using a catalyst consisting essentially of aluminum fluoride containing minor quantities of iron, chromium, and preferably nickel. The catalyst is prepared by adding iron or chromium compounds, and preferably also nickel compounds in a subdivided form to aluminum fluoride or alumina and then subjecting the composition thus obtained to an activation treatment by heating at 300° to 550° C. in a stream of nitrogen or air and then subjecting this composition to a fluorination treatment by heating at 200° to 500° C. Vecchio et al., discloses that the chromium and nickel are introduced preferably as a water solution of their salts. In a similar disclosure, British patent No. 1,283,386, Groppelli et al., published July 26, 1972, discusses a catalyst consisting of aluminum fluoride or fluorinated alumina with small quantities of manganese and chromium compounds.

U.S. Pat. No. 4,147,733, Fiske et al., issued Apr. 3, 1979, discloses the reaction of halogenated ethanes and ethylenes with hydrogen fluoride in the vapor phase in the presence of steam in the presence of an alumium fluoride, a nickel fluoride, or a chromium fluoride, or mixture thereof. The catalysts are thought to be oxyfluorides or hydroxyfluorides.

European Patent Publication No. 0 042 696, published Nov. 16, 1983, discloses the preparation of trifluoromethylpyridines using as a catalyst a fluoride of aluminum, chromium, iron, nickel, manganese, or cobalt. The Patent Publication states that it is preferred to charge a metallic oxide, chloride, hydroxide, or carbonate and to convert it into a fluoride with anhydrous hydrogen fluoride.

Japanese OPI No. 16,943/85, published Jan. 28, 1985, discloses the preparation of fluoromethane by the vapor reaction of methyl chloride and hydrogen fluoride in the presence of chromium fluoride and aluminum fluoride.

European Patent Publication No. 0 074 069, published Jan. 8, 1986, discloses the preparation of chlorofluoromethylbenzene using as a catalyst an aluminum fluoride carrying salts of iron, bismuth, tin, as well as chromium oxide or partially fluorinated chromium oxide carrying an alkali metal fluoride. The aluminum fluoride is immersed in an aqueous solution of the salt to be carried. After immersion the aluminum fluoride is heated to a temperature from 100° to 150° C. and preferably treated with hydrogen fluoride under reaction conditions.

The preparation of TFP from 1,1,1,3-tetrachloropropane, using HF as the fluorinating agent is at least a two-step process where, in addition to a fluorination reaction, dehydrohalogenation of the propane to a propene must occur. Thus, expansion of the art to fluorination of chlorinated hydrocarbons in general may be inappropriate.

Nowhere in the art is there demonstrated or suggested a catalyst for the preparation of 3,3,3-trifluoropropene-1 which is produced by mechanical mixing. in the absence of water, of aluminum fluoride and a transition metal compound, the transition metal compound being converted to a transition metal fluoride upon contact with anhydrous hydrogen fluoride.

SUMMARY OF THE INVENTION

The objective of the instant invention is to provide a more efficient catalyst for the preparation of 3,3,3-trifluoropropene-1 (TFP) from the vapor phase reaction of a 1,1,1,3-tetrahalopropane with anhydrous hydrogen fluoride (HF). A further objective of the instant invention is to provide a simpler, less costly manufacturing procedure for the preparation of such an improved catalyst.

The instant invention is based upon the finding that a simple mechanical mixture of aluminum fluoride with a transition metal compound and the treatment of the mixture with anhydrous HF yields a more effective catalyst for the preparation of TFP via this chemical route than was previously known in the art. A subsequent finding is that the instant invention is only effective with aluminum fluoride material that has not been subjected to temperatures above about 500° C. during its preparation. The inventors believe that it is also preferable to utilize aluminum fluoride materials that originate from hydrated aluminum fluoride. As shown in the examples, infra, aluminum fluoride alone or a transition metal compound. such as a chloride of iron alone, are not effective as catalysts for the TFP process of the instant invention.

Much of the prior art in the preparation of TFP deals with the preparation of fluorination catalyst via "wet" or aqueous processes. In such processes aluminum fluoride or alumina are impregnated with an aqueous solution of the desired metal compound. The conversion of the alumina or metal compound to fluoride-containing material is normally effected by heat and the presence of HF. The very corrosive nature of HF, and particularly aqueous HF, requires very expensive corrosion-resistant equipment and specialized processing to account for this corrosiveness. Thus, the instant invention greatly simplifies processing and significantly reduces manufacturing costs.

Chromium materials are favored in the art as additive metals to catalysts for the preparation of TFP from halogenated propanes. It has been found in the instant invention that a wider range of metal compounds may be utilized. Further, the use of less expensive metal compounds such as iron compounds further improve the economics of TFP preparation.

DESCRIPTION OF THE INVENTION

In accordance with the instant invention there is provided a process for the preparation of an improved catalyst for the preparation of 3,3,3-trifluoropropene-1 (TFP) from the reaction between anhydrous hydrogen fluoride (HF) and a halogenated propane, the details of which will be delineated herein. What is described, therefore, is a process for preparing a catalyst, said process comprising (A) providing aluminum fluoride, said aluminum fluoride having been prepared at a temperature less than about 500° C.;

(B) mechanically mixing, without water, the aluminum fluoride with a transition metal compound selected from a group consisting of compounds of cobalt, chromium, iron, manganese, nickel, titanium, and vanadium; and (C) contacting the mechanical mixture of aluminum fluoride and the transition metal compound with sufficient gaseous anhydrous hydrogen fluoride to convert the transition metal compound to a transition metal fluoride.

The aluminum fluoride should be material that has been processed, such as being dried, at a temperature less than about 500° C. This is a temperature above which, the inventors believe, the physical form and chemical form of the aluminum fluoride are altered to the detriment of the benefits of the improved catalyst. It is preferred that the aluminum fluoride be processed at a temperature at about 400° C. or less. The aluminum fluoride can be anhydrous aluminum fluoride. Preferably, the starting aluminum fluoride should be hydrated aluminum fluoride to assure that during processing to remove water, processing temperatures have not exceeded 400° C. The examples, supra, demonstrate an apparent relationship between catalyst surface area and effectiveness of the catalyst in the preparation of TFP. The inventors submit that catalyst surface area is a direct result of aluminum fluoride surface area and that surface area is a function of temperature. Use of commercial anhydrous aluminum fluoride, which the inventors submit is calcined at temperatures greater than 1000° C., resulted in a catalyst with low surface area and poor performance as a catalyst for the preparation of TFP.

For the purposes of the instant invention, the term "transition metal" means transition metals of Period 4 of the Periodic Table of Elements. The transition metal compound is selected from a group consisting of compounds of cobalt, chromium, iron, manganese, nickel, titanium, and vanadium. Preferably. the transition metal compound is selected from a group consisting of compounds of cobalt, chromium, iron, and nickel. More preferably the transition metal compound is an iron compound. Preferably the iron compound is a chloride of iron or an oxide of iron.

When hydrated aluminum fluoride is utilized, water removal should be carried out at a temperature less than about 400° C. Water of hydration of the aluminum fluoride can be removed before mechanical mixing with the transition metal compound. Water of hydration can be removed after mechanically mixing with the transition metal compound or during contact of the mechanical mixture with anhydrous hydrogen fluoride.

Mechanical mixing, without water, of the aluminum fluoride and the transition metal compound can be effected by known means for dry solids blending, such as mechanically agitated mixers, tumblers, fluidized bed mixers, and mills.

The mixture of the aluminum fluoride and the transition metal compound should be contacted with a sufficient quantity of anhydrous HF to essentially convert all of the transition metal compound to a transition metal fluoride. A "sufficient quantity" of anhydrous HF is a several-fold excess, as an example, a ten-fold excess, over the stoichiometric excess of HF needed to convert the transition metal compound to a transition metal fluoride. Contact of the mechanical mixture with excess HF should occur over a period for example, of greater than about one hour. The mechanical mixture of aluminum fluoride and the metal compound should preferably be heated to a temperature greater than about 150° C. in the presence of anhydrous HF. Contacting the mixture of aluminum fluoride and the transition metal compound with anhydrous HF can be effected as a separate process step in conventional gas/solids devices, such as agitated blenders, fluidized bed mixers, and the like. The contact device should have provisions for heating and cooling. Additionally. the contact device should have provisions for handling the effluent water and HF generated in the drying and treatment of the solids with HF. The mixture of aluminum fluoride and the metal compound may also be contacted with HF in the reactor for the preparation of TFP.

In accordance with the instant invention there is also provided an improved catalyst for the preparation of 3,3,3-trifluoropropene-1 (TFP) from the reaction between anhydrous hydrogen fluoride (HF) and a halogenated propane, the details of the catalyst delineated herein. What is described, therefore, is a catalyst composition prepared according to the process described above.

The catalyst of the instant invention is a mechanical mixture of aluminum fluoride and a solid transition metal compound. As such, there is no need for water or aqueous HF. The aluminum fluoride and the transition metal compound are described, supra.

The transition metal compound should be present in the catalyst composition in an amount such that the transition metal content of the transition metal compound is greater than about 1 percent of the catalyst weight. Preferably, the transition metal content should be in a range from about 1 to 9 weight percent of the catalyst weight. The limits for transition metal content of the catalyst define a range over which there exists a balance among maximum conversion of 1,1,1,3-tetrahalopropane to TFP, maximum reaction cycle time before regeneration is necessary, and maximum catalyst life.

Finally, in accordance with the instant invention there is provided a process for the preparation of 3,3,3-trifluoropropene-1 using the catalyst of the instant invention under conditions delineated herein. What is described, therefore, is a process for the preparation of 3,3,3,-trifluoropropene-1, said process comprising
(A) feeding a 1,1,1,3-tetrahalopropane, having the formula,

wherein each X is independently selected from a group consisting of chlorine and bromine atoms, and a stoichiometric excess of anhydrous hydrogen fluoride relative to the 1,1,1,3-tetrahalopropane to a reactor containing a catalyst comprising
  (i) aluminum fluoride, said aluminum fluoride having been prepared at a temperature less than about 500° C.; and
  (ii) a transition metal compound selected from a group consisting of compounds of cobalt, chromium, iron, manganese, nickel, titanium, and vanadium, said transition metal compound being mechanically mixed without water with the aluminum fluoride, and said mixture of aluminum fluoride and the transition metal compound being treated with sufficient gaseous anhydrous hydrogen fluoride to convert the metal compound to a metal fluoride;
(B) contacting said 1,1,1,3-tetrahalopropane with said anhydrous hydrogen fluoride in the presence of said catalyst at a temperature above about 200° C.;
(C) effecting reaction of the 1,1,1,3-tetrahalopropane with the anhydrous hydrogen fluoride; and
(D) recovering the 3,3,3-trifluoropropene-1 from the mixture from (C).

The reaction of a 1,1,1,3-tetrahalopropane with anhydrous HF in the vapor phase at an elevated temperature in contact with the catalyst of the instant invention is at least a two-step process in which the tetrahalopropane is dehydrohalogenated, forming a propene, and the remaining halogen groups, chlorine or bromine, are fluorinated to yield 3,3,3-trifluoropropene-1. A hydrogen halide, either hydrogen chloride or hydrogen bromide, is the by-product of the reaction. A minor portion of the tetrahalopropane is decomposed to carbonaceous material which deposits on the catalyst surface.

The 1,1,1,3-tetrahalopropane can be, for example, 1,1,1,3-tetrachloropropane, 1,1,1,3-tetrabromopropane, 1-bromo-1,1,3-trichloropropane, 1,1-dibromo-1,3-dichloropropane, 1,1,1-tribromo-3-chloropropane, and 1-chloro-1,1,3-tribromopropane, The preferred tetrahalopropane is 1,1,1,3-tetrachloropropane.

The stoichiometric amount of anhydrous HF relative to a 1,1,1,3-tetrahalopropane to produce TFP is 3 moles of HF per mole of tetrahalopropane. A stoichiometric excess of HF of greater than about 100 percent, 6 moles HF per mole of tetrahalopropane, is preferred to maximize conversion of the tetrahalopropane to TFP and to facilitate regeneration of the catalyst and retention of catalytic activity. A more preferred stoichiometric excess is in a range from about 100 to 300 percent, 6 to 18 moles HF per mole of tetrahalopropane. Lower stoichiometric excesses may be utilized; however, more decomposition of the tetrahalopropane to carbonaceous material that deposits on and fouls the catalyst results. Higher stoichiometric excesses result in undue dilution of the tetrahalopropane and reduced production rates.

The description of the catalyst is presented, supra.

The 1,1,1,3-tetrahalopropane and the HF should be contacted and allowed to react in the presence of the catalyst at a temperature of greater than about 200° C. Preferably the contact and reaction temperature should be in a range from about 250° C. to 350° C. These temperature limits are presented as a balance between sufficient reactivity for maximum conversion of the tetrahalopropane to TFP and the fouling of the catalyst with carbonaceous material from the decomposition of the tetrahalopropane. Lower and higher temperature may be employed; however, the benefits of the instant invention may be reduced.

The time period over which the 1,1,1,3-tetrahalopropane and HF are contacted with the catalyst at a temperature greater than about 200° C. should be greater than about 0.1 second. More preferably the contact time should be in a range from about 1 to 10 seconds. This is a range of contact time over which the desired conversion of tetrahalopropane to TFP of greater than 90 percent is maintained. Additionally, contact time greater than 10 seconds increases the decomposition of the tetrahalopropane and fouling of the catalyst.

Contacting the tetrahalopropane and the HF in the presence of the catalyst and effecting reaction to form TFP can be carried out in known gas-solid reactor configurations, such as a fluid bed reactor, a stirred bed reactor, a vibrating bed reactor, or a fixed bed reactor. The reactor should be provided with means for heating and cooling the reactor system. Conventional means for heating and cooling could be a liquid or gas passed through a jacket surrounding the reactor or a heat exchanger within the catalyst bed. The reaction system should also be provided with means for handling of the by-produced hydrogen halide. Hydrogen halide handling can be such conventional means as a water scrubber tied together with means for neutralizing the resultant acid.

3,3,3-trifluoropropene-1 is a gas at ambient temperatures. Therefore, recovering the TFP can be effected by such known means as the procedure of cooling the gas by conventional heat exchange, compressing of the cooled gas, and cooling the compressed gas to condense the TFP as a liquified gas.

The vapor phase reaction of a 1,1,1,3-tetrachloropropane with HF at elevated temperatures results in the fouling of the catalyst with deposits of carbonaceous material. For a catalyst to be commercially viable, the carbon must be periodically treated with air or oxygen at temperature at or about 400° C. to remove the carbon as carbon dioxide. The need for regeneration of the catalyst surface requires that the process further comprise (E) periodically interrupting the feeds of 1,1,1,3-tetrahalopropane and anhydrous hydrogen fluoride to the reactor;

(F) passing an oxygen-containing stream through the reactor and the catalyst at a temperature of about 400° C. to effect oxidation of carbon deposits on the catalyst, driving off the carbon as carbon dioxide; an (G) resuming (A) through (D).

Care must be taken to prevent this exothermic oxidation reaction from causing temperatures to exceed 400° C. too greatly. Excessive temperature can reduce catalyst effectiveness. Control of the flow of the oxygen-containing stream or stepwise raising of regeneration temperature are examples of means for controlling the ultimate regeneration temperature.

A measure of catalyst effectiveness in producing 3,3,3-trifluoropropene-1 is the length of time which the reactor system may be operated before regeneration is necessary. In the instant invention sustained reaction cycle times up to 11 to 15 hours have been demonstrated. This performance can be compared to a sustained reaction cycle of 2 to 6 hours for a known fluorination catalyst, as demonstrated in an example, infra.

The reaction system should be provided with a system to regenerate the catalyst and to remove the deposited carbonaceous material. The system should include a conventional flow control system to feed the necessary air or other oxygen-containing streams to the catalyst bed. Provisions should be made to preheat the regenerating gas being fed to the catalyst bed. Temperature control should be provided to prevent heating of the catalyst bed to temperatures greater than 400° C. Means for monitoring the carbon dioxide content of the regeneration gas exiting the catalyst bed may be provided to determine the time at which regeneration has been completed.

So that those skilled in the art may better understand and appreciate the instant invention, the following examples are presented. These examples are presented to be illustrative and are not to be construed as limiting the claims herein.

EXAMPLE 1

(Not within the scope of the instant invention)

An apparatus to study the vapor-phase fluorination of 1,1,1.3-tetrachloropropane (TCP) was assembled. The apparatus consisted of (1) a feed system capable of delivering constant streams of gaseous hydrogen fluoride (HF) and TCP vapor; (2) a nickel stirred reactor, resistant to HF at temperature of 300° to 400° C.; and (3) a gas chromatographic (GC) analyzer to continuously sample and monitor the reactor effluent. The HF feed system consisted of HF cylinders in a heated cabinet to provide HF gas under pressure. The pressurized HF gas was fed and controlled by conventional flow control means. The TCP feed system consisted of a conventional positive displacement pump and a vaporizer to convert the liquid TCP to a vapor. The TCP vapor and HF gas were preheated before entering the reactor. The reactor was a conventional agitated reactor, capable of mixing a solid, particulate material. The reactor was electrically heated, with conventional temperature control to maintain desired temperature within the reactor. The reactor effluent passed through a filter to remove traces of catalyst from the effluent gases. A backpressure valve was used in the gas vent line to maintain sufficient pressure to pass vapor samples through the gas chromatographic analyzer.

In a typical catalyst evaluation run, about 300 g of the catalyst was charged to the reactor. The catalyst and the reactor were heated to 400° C. under a nitrogen purge. The nitrogen purge was continued for about 30 minutes. Gaseous HF was then used to purge the reactor in place of nitrogen. The reactor was then cooled to the desired reaction temperature. HF feed was stabilized, and then the TCP pump was started at the desired flow rate.

Feeds continued until the conversion of TCP to the desired 3,3,3-trifluoropropene-1 (TFP), as determined by the GC analyzer. fell below 90 percent. The TCP feed was shut off, and the HF feed continued for an additional 15-20 minutes and was then turned off. A nitrogen purge was turned on, and the reactor temperature was raised to 350° C. The nitrogen purge was turned off, and then air was introduced to the reactor to oxidize carbonaceous material that had deposited on the catalyst surface. After one hour at 350° C. the heat was increased to raise the reactor temperature to 400° C. The air flow was continued at 400° C. for 4-6 hours. At this point the fluorination-regeneration cycle was complete.

To establish a benchmark for catalyst evaluation, a fluorination catalyst, similar to that described in British Pat. No. 823,519, published Nov. 11, 1959, was used to produce TFP. This catalyst was prepared by impregnating alumina with an aqueous solution of cobalt chloride. This wet mixture was saturated with HF. This mixture was then dried by heating in an HF atmosphere.

In this evaluation, 300 g of a catalyst prepared above was placed in the reactor. Reaction temperature was 250° C. This catalyst had a cobalt content of 3.2 weight percent. TCP feed rate was controlled at 76.7 g/hr; and HF feed was controlled at 70.2 g/hr, an 8.4/1 mole ratio of HF/TCP. From the above, a residence time in the bed of catalyst of about 7 seconds is calculated. Four successive reaction/regeneration cycles were carried out. This series of runs is designated as Sample A. Each reaction cycle was continued until the conversion of TCP to TFP fell below 90 percent, according to GC analysis. Table 1 is a summary of the length of time for each reaction cycle to fall below 90 percent. The cycle number in Table 1 is designated "Cycle"; and the time in hours to fall below 90 percent is designated as "Time".

TABLE 1

| Sample | Cycle | Time |
|---|---|---|
| A | 1 | 6.5 |
|   | 2 | 4.3 |
|   | 3 | 4.0 |
|   | 4 | 2.6 |

The above results demonstrate the performance of a known catalyst for the preparation of TFP from the vapor-phase reaction of TCP with anhydrous HF.

EXAMPLE 2

Using the apparatus and procedures of Example 1, several series of runs were made to evaluate mechanical mixtures of aluminum fluoride and various transition metal chlorides as catalysts for the fluorination of TCP to form TFP.

The aluminum fluoride was prepared by the reaction of aluminum hydroxide with aqueous HF. In a Teflon ® beaker 400 g of aqueous HF (47-52 percent by weight in water) was diluted with 1600 ml of water. The HF solution was stirred with a magnetic stirring bar and heated to 60° C. To the HF solution was slowly added 200 g of aluminum hydroxide. The aluminum hydroxide was added slowly to maintain the temperature of the reactants at 60° C. The aluminum hydroxide dissolved, producing a clear solution. The solution was heated overnight at 60° C. During this time, crystalline material was formed. The solid was isolated by decanting the aqueous material and drying on filter paper. The solids were then dried for 4 hours at 100° C. in a vacuum oven. The solids were then dried overnight at 400° C. in an air circulating oven. Analysis of the solids by X-ray diffraction indicated the presence of alpha-aluminum fluoride with fairly small crystallite size. The aluminum hydroxide and HF used in this preparation are commercially available materials.

The mixture of aluminum fluoride with the metal chlorides was made by simple dry-mixing (shaking) of the two powders in a bottle. In some instances the metal salts were coarse and lumpy and a mortar and pestle was used to break down the solids. In these runs the amount of the transition metal chloride added to the aluminum fluoride was controlled so that the transition metal content (i.e., cobalt, chromium, copper, nickel, or iron) of the catalyst was 3,2 weight percent. The mechanical mixture of aluminum fluoride and a transition metal compound was placed in the reactor and heated to 250° C. HF was passed through the heated catalyst for about 1 hour. The temperature of the catalyst bed was raised to 400° C., and HF feed continued for about another 1 hour. The catalyst was then cooled to 250° C. under a nitrogen purge.

Similar reaction temperature and feed conditions as those in Example 1 were utilized. Table 2 is a summary of these runs which will be designated Samples B, C, D, E, and F, respectively. Table 2 utilizes the same designations used in Example 1. Additionally, Table 2 identifies the transition metal compound used in the mechanical mixture with aluminum fluoride; the transition metal chlorides are designated as "Compound".

TABLE 2

| Sample | Compound | Cycle | Time |
|---|---|---|---|
| B | $CoCl_2$ | 1 | 0.1 |
|   |   | 2 | 6.0 |
|   |   | 3 | 6.8 |
|   |   | 4 | 6.5 |
| C | $CrCl_3$ | 1 | 0.1 |
|   |   | 2 | 5.0 |
|   |   | 3 | 5.1 |
|   |   | 4 | 5.0 |
| D | $CuCl_2$ | 1 | 0.1 |
|   |   | 2 | 2.8 |
|   |   | 3 | 2.0 |
|   |   | 4 | 1.2 |
| E | $NiCl_2$ | 1 | 0 |
|   |   | 2 | 8.2 |
|   |   | 3 | 4.8 |
|   |   | 4 | 3.8 |
| F | $FeCl_3$ | 1 | 34.5 |
|   |   | 2 | 12.5[a] |
|   |   | 3 | 11.0[a] |
|   |   | 4 | 11.0[a] |

[a] HF/TCP mole ratio = 6/1

The above results demonstrate the performance of the mechanical mixture of aluminum fluoride and a metal compound as a catalyst for the vapor-phase preparation of TFP.

EXAMPLE 3

(Not within the scope of the instant invention)

Using the apparatus and procedures of Example 1, two series of runs were made to evaluate aluminum fluoride and iron chloride, respectively, as catalysts for the fluorination of TCP to form TFP.

The aluminum fluoride utilized is the same as evaluated in Example 2. The iron chloride (FeCl₃) is a commercially available reagent.

Similar temperature and feed conditions as those in Example 1 were utilized. Table 3 is a summary of these runs which will be designated Samples G and H, respectively. Table 3 utilizes the same designations used in Example 1. Additionally, Table 3 identifies the catalyst utilized; the catalysts are designated as "Catalyst".

TABLE 3

| Sample | Catalyst | Cycle | Time |
|---|---|---|---|
| G | AlF₃ | 1 | 0 |
|   |   | 2 | 0 |
|   |   | 3 | 2.0 |
| H | FeCl₃ | 1 | 0.5 |
|   |   | 2 | 0 |

The above results demonstrate the poor performance of aluminum fluoride or a metal chloride, used separately, as catalysts for the preparation of TFP.

EXAMPLE 4

(Not within the scope of the instant invention)

Several series of runs were made to evaluate the use of anhydrous aluminum fluoride, commercially available and utilized in the aluminum industry as a flux. The apparatus and procedures of Example 1 were used to evaluate anhydrous aluminum fluoride alone or in mechanical mixtures with metal compounds as catalysts for the fluorination of TCP to form TFP. These commercial anhydrous aluminum fluoride samples appeared to be calcined materials that may have been dried at temperatures in excess of 1000° C.

Similar temperature and feed conditions as those in Example 1 were utilized. Table 4 is a summary of these runs which will be designated Samples J, K, L, and M, respectively. Table 4 utilizes the same designations used in the preceding examples. Additionally, Table 4 identifies the source of the anhydrous aluminum fluoride, which is designated as "Source".

TABLE 4

| Sample | Source | Compound | Cycle | Time |
|---|---|---|---|---|
| J | Kaiser | None | 1 | 0 |
|   |   |   | 2 | 0.1 |
|   |   |   | 3 | 0.5 |
|   |   |   | 4 | 0 |
| K | Kaiser | CoCl₂ | 1 | 0.1 |
|   |   |   | 2 | 0.1 |
|   |   |   | 3 | 0.1 |
| L | Kaiser | FeCl₃ | 1 | 0.1 |
|   |   |   | 2 | 0.4 |
|   |   |   | 3 | 1.0 |
| M | Alcan | CoCl₂ | 1 | 0 |
|   |   |   | 2 | 0 |

The above results demonstrate the poor performance of aluminum fluoride which has been processed at high temperatures to drive off water.

EXAMPLE 5

Two series of runs were carried out to evaluate the use of commercially available hydrated aluminum fluoride in a mechanical mixture with an iron compound. The hydrated aluminum fluoride evaluated was a trihydrate purchased from American Hoechst, an American distributor for Reidel de Hoen of Germany. The apparatus and procedures of Example 1 were utilized.

Two catalyst samples were prepared; and are designated Samples N and P, respectively. Sample N was prepared by first mechanically mixing the hydrated aluminum fluoride with FeCl₃. The mixture was then dried in an oven for 3 days at 180° C. The mixture was then placed in the fluorination reactor in which the temperature was increased from 150° C. to 400° C. over a period of about 5 hours under a purge of HF gas. The catalyst mixture was then held at 4 hours at 400° C. under a nitrogen purge.

Sample P was a mechanical mixture of the trihydrated aluminum fluoride and iron oxide (Fe₂O₃). The Fe₂O₃ was purchased under the brand name of Mapico Red ® (Columbian Chemicals, Tulsa, Oklahoma). The mixture was placed in the fluorination reactor and purged with nitrogen. The temperature of the reactor was raised from 180° to 400° C. over a period of 6 hours. The reactor temperature was then set at 250° C. and HF was passed over the mixture for several hours to convert the Fe₂O₃ to FeF₃.

In both sample M and P the iron content was about 3 weight percent.

Similar temperature and feed conditions as those in Example 1 were utilized. Table 5 is a summary of these two runs. Table 5 utilizes the same designations used in the preceding examples.

TABLE 5

| Sample | Cycle | Time |
|---|---|---|
| N | 1 | 13.5 |
|   | 2 | 12.5 |
|   | 3 | 13.2 |
| P | 1 | 15.5 |
|   | 2 | 12.8 |
|   | 3 | 14.0 |
|   | 4 | 7.8[b] |
|   | 5 | 12.0 |
|   | 6 | 13.8 |

[b]Reaction temperature = 200° C.

The above results demonstrate that an oxide of iron works equally as well as does a chloride of iron as a mechanical mixture with aluminum fluoride as a catalyst for the preparation of TFP.

EXAMPLE 6

Samples of catalysts used in the preceding samples were analyzed for surface area and pore volume by known analytical techniques. The samples analyzed from the above were Samples A, B, F, K, and N. Table 6 is a summary of the resulting analytical results. Surface area, designated as "S.A." in Table 6 is expressed as square meters per gram (m²/g). Pore volume, designated in Table 6 as "P.V.", is expressed as cubic centimeter per gram (cc/g).

TABLE 6

| Sample | S.A. | P.V. |
|---|---|---|
| A | 23 | 0.02 |
| B | 42 | 0.04 |
| F | 49 | 0.07 |
| K | 4 | — |
| N | 57 | 0.02 |

Applying the results of surface area determinations to the results of the preceding examples demonstrates that catalysts, that is aluminum fluoride, with higher surface areas perform more favorably as catalysts for the preparation of TFP.

EXAMPLE 7

A series of runs was made to evaluate the impact of various iron loadings on the subject catalyst. The apparatus and procedures of Example 1 were utilized.

The aluminum fluoride utilized was similar to that prepared in Example 2. The iron compounds utilized were ferric chloride and ferric oxide. Mechanical mixtures of aluminum fluoride with iron content of from about 1 to 10 percent by weight of the total catalyst were prepared.

Four series of runs, designated Samples Q, R, S, and T, respectively, were carried out. Table 7 is a summary of these series of runs. The notation utilized in Table 2 of Example 2 are utilized. Additionally, the iron content of the catalyst is in weight percent, and designated as "Wt %" in Table 7 is reported.

TABLE 7

| Sample | Compound | Wt % | Cycle | Time |
|---|---|---|---|---|
| Q | FeCl$_3$ | 9.6 | 1 | 5.9$^c$ |
|   |   |   | 2 | 3.1$^c$ |
|   |   |   | 3 | 3.2$^c$ |
|   |   |   | 4 | 11.5 |
|   |   |   | 5 | 11.0 |
| R | FeCl$_3$ | 6.4 | 1 | 10.0$^c$ |
|   |   |   | 2 | 11.0$^c$ |
|   |   |   | 3 | 14.0 |
|   |   |   | 4 | 10.4 |
| S | Fe$_2$O$_3$ | 3.2 | 1 | 8.1 |
|   |   |   | 2 | 12.5 |
|   |   |   | 3 | 9.5 |
|   |   |   | 4 | 3.0 |
| T | Fe$_2$O$_3$ | 1.5 | 1 | 6.2 |
|   |   |   | 2 | 10.5 |
|   |   |   | 3 | 4.8 |

$^c$HF/TCP ratio = 6/1

The above results demonstrate the impact of iron content of the catalyst upon the TFP reaction.

What is claimed is:

1. A process for preparing a catalyst, said process comprising
   (A) providing aluminum fluoride, said aluminum fluoride having been prepared at a temperature less than about 500° C.;
   (B) mechanically mixing, without water, the aluminum fluoride with a transition metal compound selected from a group consisting of compounds of cobalt, chromium, iron, manganese, nickel, titanium, and vanadium; and
   (C) contacting the mechanical mixture of aluminum fluoride and the transition metal compound with sufficient gaseous anhydrous hydrogen fluoride to convert the transition metal compound to a transition metal fluoride, said mechanical mixture being heated to a temperature greater than about 150° C. in the presence of anhydrous hydrogen fluoride.

2. A process according to claim 1, wherein the aluminum fluoride has been prepared at a temperature of 400° C. or less.

3. A process according to claim 1, wherein the aluminum fluoride is anhydrous aluminum fluoride.

4. A process according to claim 1, wherein the aluminum fluoride is hydrated aluminum fluoride.

5. A process according to claim 4, wherein water of hydration is removed from the hydrated aluminum fluoride by heating the hydrated aluminum fluoride to a temperature sufficient to essentially remove all water of hydration, but less than about 400° C., prior to the mechanical mixing of the aluminum fluoride with the metal compound.

6. A process according to claim 4, wherein water of hydration is removed from the hydrated aluminum fluoride by heating the hydrated aluminum fluoride to a temperature sufficient to essentially remove all water of hydration, but less than about 400° C., after the mechanical mixing of the aluminum fluoride with the metal compound.

7. A catalyst composition prepared according to the process of claim 1.

8. A catalyst composition according to claim 7, wherein the aluminum fluoride is anhydrous aluminum fluoride.

9. A catalyst composition according to claim 7, wherein the aluminum fluoride is hydrated aluminum fluoride.

10. A catalyst composition according to claim 7, wherein the transition metal compound is selected from a group consisting of compounds of cobalt, chromium, iron, and nickel.

11. A catalyst composition according to claim 10, wherein the transition metal compound is a compound of iron.

12. A catalyst composition according to claim 7, wherein the transition metal compound is present in an amount in said catalyst composition such that transition metal content of the transition metal compound is greater than about 1 weight percent of catalyst weight.

13. A catalyst composition according to claim 12, wherein the transition metal compound is present in an amount in said catalyst composition such that transition metal content of the transition metal compound is in a range from about 1 to 9 weight percent of catalyst weight.

14. A catalyst composition according to claim 7, wherein the metal compound is cobalt (II) chloride.

15. A catalyst composition according to claim 7, wherein the metal compound is chromium (III) chloride.

16. A catalyst composition according to claim 7, wherein the metal compound is iron (III) chloride.

17. A catalyst composition according to claim 7, wherein the metal compound is iron (III) oxide.

18. A catalyst composition according to claim 7, wherein the metal compound is a nickel (II) chloride.

* * * * *

UNITED STATES PATENT AND TRADEMARK OFFICE
CERTIFICATE OF CORRECTION

PATENT NO. : 4,798,818

DATED : 1/17/89

INVENTOR(S) : William Xavier Bajzer, Robert Lewis Bixler, Jr., Michael Dwight Meddaugh, and Anthony P. Wright It is certified that error appears in the above-identified patent and that said Letters Patent is hereby corrected as shown below:

On the Title Page, under Item [19] and in Item [73], Correct spelling of inventor's name by deleting "Baizer" and inserting "Bajzer" therefore.

Signed and Sealed this

Twenty-second Day of August, 1989

Attest:

DONALD J. QUIGG

*Attesting Officer*     *Commissioner of Patents and Trademarks*